United States Patent [19]

Rubin et al.

[11] Patent Number: 5,266,465
[45] Date of Patent: Nov. 30, 1993

[54] α-1-ANTICHYMOTRYPSIN, ANALOGUES AND METHODS OF PRODUCTION

[75] Inventors: Harvey Rubin; Zhi M. Wang, both of Philadelphia; Barry S. Cooperman, Penn Valley; Norman Schecter, Philadelphia, all of Pa.

[73] Assignee: The Trustees of the University of Pennsylvania, Philadelphia, Pa.

[21] Appl. No.: 735,322

[22] Filed: Jul. 24, 1991

Related U.S. Application Data

[62] Division of Ser. No. 370,704, Jun. 23, 1989, Pat. No. 5,079,336.

[51] Int. Cl.$^5$ .............. C07K 3/00; C12P 21/02; C12N 15/09; A61K 45/05
[52] U.S. Cl. .................. 435/69.2; 435/69.1; 435/172.1; 435/172.3; 435/213; 530/350
[58] Field of Search .................. 435/69.1, 69.2, 172.1, 435/172.3, 320.1, 213; 530/380, 350

[56] References Cited

U.S. PATENT DOCUMENTS 4,732,973  3/1988  Barr et al. ..................... 530/350

OTHER PUBLICATIONS

Chandra, T. et al. "Sequence Homology between Human α1-Antichymotrypsin, α1-Antitrypsin, & Antithvombin III." *Biochem.* 22 (22): 5055–5060, (1983).
Morii, M. et al. "Amino Acid Sequence of the Reactive Site of Human α1-Antichymotrypsin." *J. Biol. Chem.* 258 (21): 12749–12752. (1983).
Studier, et al., J. Mol. Biol. 89:113–130 (1986).
Tsuda, et al., Takai, J. Exp. Clin. Med. 7:201–211 (1982).
Young, et al., Proc. Natl. Acad. Sci., USA 80:1194–1198 (1983).
Hill, et al., Nature 311:175–177 (1984).
Chandra, et al., Biochemistry 22:5055–5060 (1983).
DelMar, et al., Anal. Biochem. 99:316–320 (1979).
Ardelt, et al., Biochemistry 24:5313–5320.
Laemmli, Nature (London) 227:680–685 (1970).
Beatty, et al., J. Biol. Chem. 225:3931–3934 (1980).
Towbin, et al., Proc. Nat'l Acad. Sci USA 76:4350–4354 (1979).
Carrell and Owen, Nature 317:730–732 (1985).
Wachter, et al., "Cloning A Serine Protease Inhibitor Gene With An Antibody Specific Probe", Abstract, Jan. 1987, American Academy of Allergy and Immunology.
Wachter, et al., "Cloning And Antigenic Determinants Of Serine Protease Inhibitors", Abstract, Jan. 1987, Annals of Allergy.
Morii and Travis, J. Biol. Chem. 258:12749–12752 (1983).
Baumann et al. (1991) "Crystal Structure of Cleaved Human α$_1$-Antichymotrypsin, at 2-7 Å Resolution and Its Comparison with Other Serpins", *J. Mol. Biol.* 218:595–606.
Oliver, S. G. and Ward, J. M., *A Dictionary of Genetic Engineering,* Cambridge University Press, Cambridge, England, 1985, p. 18.
Walker, J. M. and Cox, M., *The Language of Biotechnology–A Dictionary of Terms,* American Chemical Society, Washington, D.C., 1988, p. 109.

*Primary Examiner*—Robert A. Wax
*Assistant Examiner*—Dian Cook
*Attorney, Agent, or Firm*—Woodcock Washburn Kurtz Mackiewicz & Norris

[57] ABSTRACT

The invention provides α-1-antichymotrypsin and protein preparations comprising human α-1-antichymotrypsin produced by *E. coli* cells transformed with a DNA sequence encoding human α-1-antichymotrypsin. The invention also provides methods for producing α-1-antichymotrypsin. The invention further provides analogues of α-1-antichymotrypsin that exhibit anti-chymotrypsin, anti-trypsin and anti-thrombin activity and methods of producing the analogues.

4 Claims, 6 Drawing Sheets

```
                                                10
                                                 |
                                    CTC TGC CAC CCT AAC AGC CCA CTT GAC GAG GAG AAT CTG ACC CAG GAG AAC CAA
                                    Leu Cys His Pro Asn Ser Pro Leu Asp Glu Glu Asn Leu Thr Gln Glu Asn Gln
                                            20            30            40            50
                                                                                         |
                                                 60            70            80            90           100
                                                  |             |             |             |             |
                                    GAC CGA GGG ACA CAC GTG GAC CTC GGA TTA GCC CTC AAG CAG TTA GTC CTG AAG CAG TTG GTC CTG AAG AAT GTC ATC TTC
                                    Asp Arg Gly Thr His Val Asp Leu Gly Leu Ala Leu Lys Gln Leu Val Leu Lys Asn Val Ile Phe
                                                                                                        150           160
                                                                                                         |             |

TTC AGC CTG TAC AAG CAG TTA GTC CTG AAG GCC CCT GAT AAG AAT GTC ATC TTC
                                    Phe Ser Leu Tyr Lys Gln Leu Val Leu Lys Ala Pro Asp Lys Asn Val Ile Phe
                                           170           180           190           200           210
                                            |             |             |             |             |
                                    TCC CCA AGC ATC GAG ATT CTC ACC GCC TTG CTG TCT CTG GGG GCC CAT AAT
                                    Ser Pro Ser Ile Glu Ile Leu Thr Ala Leu Leu Ser Leu Gly Ala His Asn
                                           220           230           240           250           260           270
                                            |             |             |             |             |             |
                                    ACC ACC CTG ACA GAG ATT CTC AAA GGC CTC AAG TTC AAC CTC ACG GAG ACT TCT
                                    Thr Thr Leu Thr Glu Ile Leu Lys Gly Leu Lys Phe Asn Leu Thr Glu Thr Ser
                                           280           290           300           310           320
                                            |             |             |             |             |
                                    GAG GCA GAA ATT CAC CAG AGC TTC CAG CAC CTC CGC ACC CTC AAT CAG TCC
                                    Glu Ala Glu Ile His Gln Ser Phe Gln His Leu Arg Thr Leu Asn Gln Ser
```

*Fig. 1a*

```
330
AGC GAT GAG CTG CAG CTG AGT ATG GGA AAT GCC ATG TTT GTC AAA GAG CAA CTC
Ser Asp Glu Leu Gln Leu Ser MET Gly Asn Ala MET Phe Val Lys Glu Gln Leu
                340         350         360         370              430
                                                                      —
380                                                                   
—                                                                     
AGT CTG CTG GAC AGG TTC ACG GAG GAT GCC AAG AGG CTG TAT GGC TCC GAG GCC
Ser Leu Leu Asp Arg Phe Thr Glu Asp Ala Lys Arg Leu Tyr Gly Ser Glu Ala
        390         400         410         420

480
                                                         —
TTT GCC ACT GAC TTT CAG GAC TCA GCT AAG GCA GCT AAG AAG CTC ATC AAC GAC TAC
Phe Ala Thr Asp Phe Gln Asp Ser Ala Lys Ala Ala Lys Lys Leu Ile Asn Asp Tyr
    440         450         460         470

490                                                                       540
—                                                                         —
GTG AAG AAT GGA ACT AGG GGG AAA ATC ACA GAT CTG ATC AAG GAC CTT GAC TCG
Val Lys Asn Gly Thr Arg Gly Lys Ile Thr Asp Leu Ile Lys Asp Leu Asp Ser
        500         510         520         530

590
                                                                  —
CAG ACA ATG ATG GTC CTG AAT TAC ATC TTC TTT AAA GCC AAA TGG GAG ATG
Gln Thr MET MET Val Leu Asn Tyr Ile Phe Phe Lys Ala Lys Trp Glu MET
    550         560         570         580

600                                                                  640
—                                                                    —
CCC TTT GAC CCC CAA GAT ACT CAT CAG TCA AGG TTC TAC TTG AGC AAA AAG
Pro Phe Asp Pro Gln Asp Thr His Gln Ser Arg Phe Tyr Leu Ser Lys Lys Lys
        610         620         630
```

Fig. 1b

```
650—
TGG GTA ATG GTG CCC ATG ATG AGT TTG CAT CAC CTG ACT ATA CCT TAC TTC CGG
Trp Val MET Val Pro MET MET Ser Leu His His Leu Thr Ile Pro Tyr Phe Arg
                 660—              670—              680—              690—              700—

GAC GAG CTG TCC TGC ACC GTG GTG GAG CTG AAG TAC ACA GGC AAT GCC AGC
Asp Glu Leu Ser Cys Thr Val Val Glu Leu Lys Tyr Thr Gly Asn Ala Ser
    710—              720—              730—              740—              750—

GCA CTC TTC ATC CTC CCT GAT CAA GAC AAG ATG GAG GAA GTG GAA GCC ATG CTG
Ala Leu Phe Ile Leu Pro Asp Gln Asp Lys MET Glu Glu Val Glu Ala MET Leu
760—              770—              780—              790—              800—              810—

CTC CCA GAG ACC CTG AAG CGG TGG AGA GAC TCT CTG GAG TCC ATC TCG AGG GAC TAT AAC GAC ATA GGT
Leu Pro Glu Thr Leu Lys Arg Trp Arg Asp Ser Leu Glu Ser Ile Ser Arg Asp Tyr Asn Asp Ile Gly
    820—              830—              840—              850—              860—

GAG CTC TAC CTG CCA AAG TTT TCC ATC TCG AGG GAC TAT AAC GAC ATA
Glu Leu Tyr Leu Pro Lys Phe Ser Ile Ser Arg Asp Tyr Asn Asp Ile
    870—              880—              890—              900—              910—

CTT CTC CAG CTG GGC ATT GAG GAA GCC TTC ACC AGC AAG GCT GAC CTG TCA GGG
Leu Leu Gln Leu Gly Ile Glu Glu Ala Phe Thr Ser Lys Ala Asp Leu Ser Gly
920—              930—              940—              950—              960—              970—
```

Fig. 1c

```
980                  990                 1000                1010                1020
 —                    —                   —                   —                   —
ATC ACA AGG GCC AGG AAC CTA GCA GTC TCC CAG GTG GTC CAT AAG GCT GTG CTT
Ile Thr Gly Ala Arg Asn Leu Ala Val Ser Gln Val Val His Lys Ala Val Leu 1030                1040                1050                1060                1070                1080
        —                   —                   —                   —                   —                   —
GAT GTA TTT GAG GAG GGC ACA GAA GCA TCT GCT GCC ACA GTC AAA ATC ACC
Asp Val Phe Glu Glu Gly Thr Glu Ala Ser |Ala Ala|Thr Ala Val Lys Ile Thr
                                         349 350

1090                1100                1110                1120                1130
               —                   —                   —                   —                   —
CTC CTT TCT GCA TTA GTG GAG ACA AGG ACC ATT|GTG CGT|TTC AAC AGG CCC TTC
Leu Leu Ser Ala Leu Val Glu Thr Arg Thr Ile|Val Arg|Phe Asn Arg Pro Phe
 P₁  P₁'                                     368 369

1140                1150                1160                1170                1180
        —                   —                   —                   —                   —
CTG ATG ATC ATT GTC CCT ACA GAC ACC CAG AAC ATC TTC TTC ATG AGC AAA GTC
Leu MET Ile Ile Val Pro Thr Asp Thr Gln Asn Ile Phe Phe MET Ser Lys Val 1190                1200                1210                1220                1230                1240
 —                   —                   —                   —                   —                   —
ACC AAT CCC AAG CAA GCC TAG AGC TTG CCA TCA AGC AGT GGG GCT CTC AGT AAG
Thr Asn Pro Lys Gln Ala ---  Ser Leu Pro Ser Ser Gly Ala Leu Ser Lys
```

*Fig. 1d*

```
                    1250        1260                    1270                    1280                    1290
                     |           |                       |                       |                       |
GAA CTT GGA ATG CAA GCT GGA TGC CTG GGT CTC TGG CAC AGC CTG GCC CCT GTG
Glu Leu Gly MET Gln Ala Gly Cys Leu Gly Leu Trp His Ser Leu Ala Pro Val 1300                    1310                    1320                    1330                    1340                    1350
        |                       |                       |                       |                       |                       |
CAC CGA GTG GCC ATG GCA TGT GTG GCC CTG TCT GCT TAT CCT TGG AAG GTG ACA
His Arg Val Ala MET Ala Cys Val Ala Leu Ser Ala Tyr Pro Trp Lys Val Thr 1360                    1370                    1380                    1390                    1400
                     |                       |                       |                       |                       |
GCG ATT CCC TGT GTA GCT CTC ACA TGC ACA GGG GCC CAT GGA CTC TTC AGT CTG
Ala Ile Pro Cys Val Ala Leu Thr Cys Thr Gly Ala His Gly Leu Phe Ser Leu 1410                    1420
        |                       |
GAG GGT CCT GGG CCT GGA ATT
Glu Gly Pro Gly Pro Gly Ile
```

*Fig. 1e*

α-1-ANTICHYMOTRYPSIN, ANALOGUES AND METHODS OF PRODUCTION

This is a division of application Ser. No. 370,074, filed Jun. 23, 1989, now U.S. Pat. No. 5,079,336.

FIELD OF THE INVENTION

This invention is related to the field of substances produced by recombinant DNA technology, and more particularly to the field of proteins produced by recombinant DNA technology.

BACKGROUND OF THE INVENTION

α-1-Antichymotrypsin is a serine protease inhibitor (serpin). In its native, circulating form, it is a glycoprotein of between 55,000 and 66,000 daltons, with the variation attributed to microheterogeneity in glycosylation. It is synthesized predominantly in the liver, and has also been reported in mast cells, sinus histiocytes, endothelial cells, and in cells of the histio/monocytic line. In response to inflammatory stimuli, plasma levels of α-1-antichymotrypsin increase more than four-fold within several hours.

The precise biological role of α-1-antichymotrypsin has not been determined. Based on its rapid rate of association with cathepsin G, it may regulate the activity of this neutrophil serine protease. However, other targets are also possible. Chymotrypsin-like enzymes and their inhibitors have been identified in a wide variety of normal and abnormal biological processes including: modulation of cellular functions, DNA binding, inhibition of certain parasite functions and processing of vasoconstrictor proteins. α-1-antichymotrypsin appears to be a component of the amyloid deposit in Alzheimer's plaques and is present in various carcinomas and in some tissues of the reproductive system.

Human α-1-antichymotrypsin forms SDS-stable complexes with its target enzymes, which is a general property of serpin/serine protease interactions. Little of a detailed nature is known about the nature of these complexes. Although high-resolution crystal structures of chymotrypsin and chymotrypsin/small molecular inhibitor complexes have been solved and NMR analysis of the enzyme have been reported, no direct structural studies of human α1-antichymotrypsin alone or as a complex with a serine protease have been reported.

Antithrombin III and α-1-antitrypsin are also serine protease inhibitors. Antithrombin III inactivates thrombin by forming an irreversible complex with it. Antithrombin III also inhibits clotting factors $IX_a$, $X_a$ and $XI_a$. α-1-antitrypsin inhibits tyrpsin by binding to its active site, and neutralizes any trypsin formed prematurely within the pancreatic cells or or pancreatic ducts.

There is evidence that proteases and oxidants play a central role in establishing and maintaining shock physiology, and that protease inhibitors can favorably modify the outcome of shock. Small molecule protease inhibitors have been shown to have efficacy in pancreatitis in humans. Similarly, antichymotrypsins may be implicated in treatment of coagulation disorders as in liver diseases. Proteases are also important mediators of inflammatory diseases. Regulation of these enzymes by their inhibitors are critical for the control of tissue destruction in these diseases.

Despite the availability of human α-1-antichymotrypsin from serum, quantities large enough for therapeutic uses have been unobtainable, due in large part to the limited availability of human serum. Consequently, there is a great need for other sources of α-1-antichymotrypsin to fill the needs created by therapeutic uses.

SUMMARY OF THE INVENTION

The invention provides α-1-antichymotrypsin in essentially pure form produced in *E. coli* cells transformed with a DNA segment encoding human α-1-antichymotrypsin, all of said α-1-antichymotrypsin being in unglycosylated form. The invention also provides a protein preparation comprising human-α-1-antichymotrypsin synthesized by *E. coli* transformed with a DNA segment encoding human a-antichymotrypsin, all of said α-1-antichymotrypsin being in unglycosylated form. The protein preparation preferably comprises human α-1-antichymotrypsin synthesized from a DNA segment having the sequence in FIG. 1 or an N-terminal extension of amino acids deriving from the expression systems.

The invention also provides protein analogues of α-1-antichymotrypsin. The analogues of α-1-antichymotrypsin are modified at amino acid 358 by the substitution of methionine, arginine or phenylalanine for leucine of the wild-type α-1-antichymotrypsin. Amino acid number 1 is considered to be the first Asn in the sequence in FIG. 1a; see FIGS. 1a through 1e. The invention also provides an α-1-antichymotrypsin cassette protein having unique Kpn I and Mlu I restriction sites at each end of the cassette portion.

The invention further provides methods of producing α-1-antichymotrypsin comprising the steps of culturing a microbial host cell, preferably *E. coli*, transformed with a DNA sequence encoding human α-1-antichymotrypsin in an appropriate medium, so that α-1-antichymotrypsin is produced and substantially purifying the α-1-antichymotrypsin from the host cell or the medium. The invention also provides methods of producing the α-1-antichymotrypsin analogues by culturing a host cell transformed with a DNA sequence encoding the α-1-antichymotrypsin analogue in an appropriate medium, so that α-1-antichymotrypsin analogue is produced and substantially purifying the α-1-antichymotrypsin analogue from the host cell or the medium.

Although human α-1-antichymotrypsin can be purified from serum, it is believed that for economic, large scale production of this therapeutically valuable substance, the use of recombinant DNA technology is preferred.

The α-1-antichymotrypsin of the invention is prepared in a prokaryotic host and thus is not glycosylated, as is the native human protein. Surprisingly, the unglycosylated human α-1-antichymotrypsin of the invention displays substantial functional similarity with native human serum α-1-antichymotrypsin, as disclosed herein, and should be an effective substitute for native human α-1-antichymotrypsin in therapeutic applications. Efficient production of the protein product is obtained in *E. coli* from which it may be isolated, purified and employed for a variety of therapeutic uses.

The novel α-1-antichymotrypsin analogues of the invention having methionine, phenylalanine or a cassette portion have antichymotrypsin activity and are expected to be useful in the same manner as antichymotrypsin itself. The novel α-1-antichymotrypsin analogue having arginine substituted for leucine at position 358 has anti-thrombin and anti-trypsin activity and are expected to be useful in treating blood clotting diseases and pancreatitis.

BRIEF DESCRIPTION OF THE DRAWINGS

FIG. 1a-1e shows the nucleotide sequence of α-1-antichymotrypsin as determined from an Eco RI restriction fragment.

DETAILED DESCRIPTION OF THE INVENTION

Figure 2:
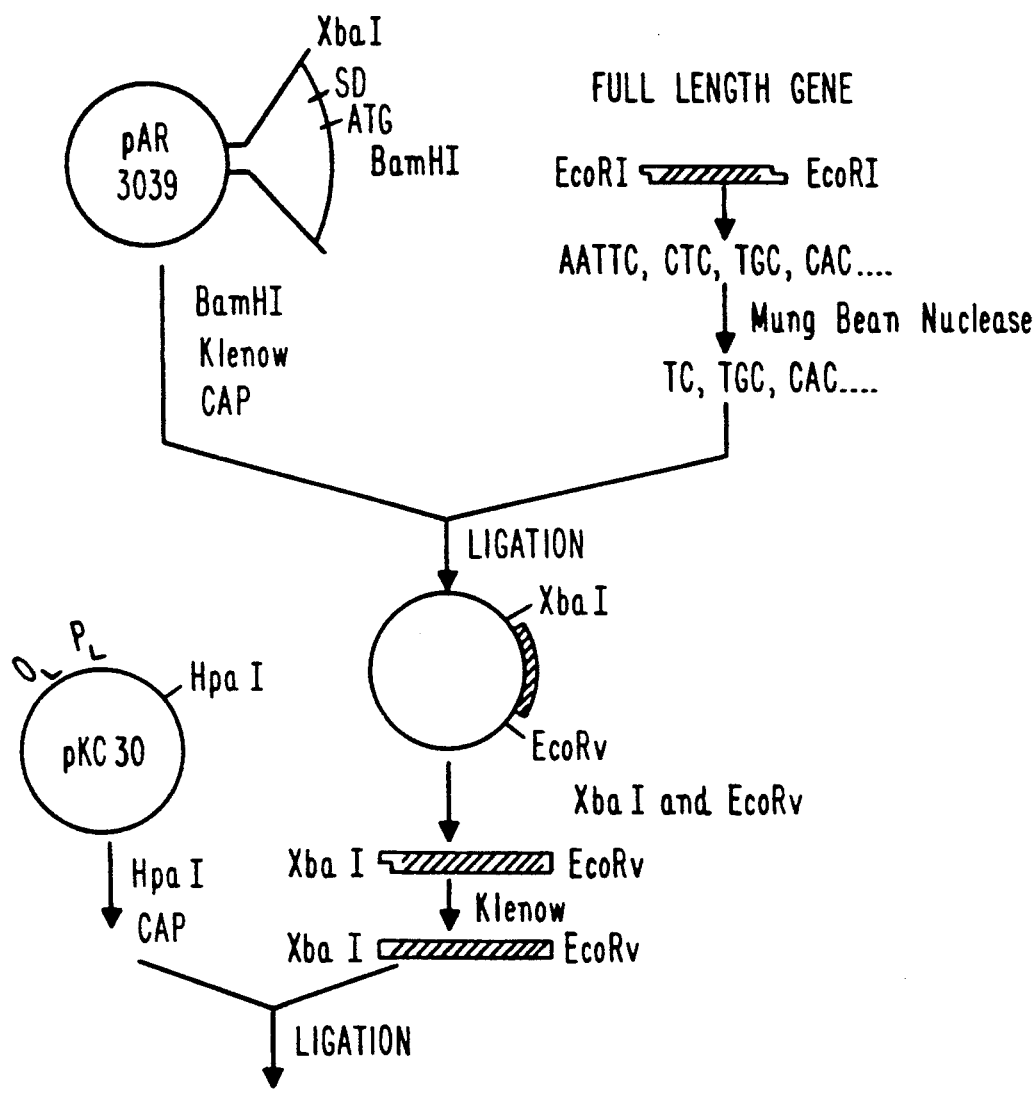
FIG. 2 shows a diagram of the steps for constructing plasmid pACT2.

Novel recombinantly produced a-1-antichymotrypsin, α-1-antichymotrypsin analogues, α-1-antichymotrpysin and α-1-antichymotrypsin analogue protein preparations and methods for producing the same are provided. Generally, α-1-antichymotrypsin the α-1-antichymotrypsin analogues are produced in host cells that have been transformed with an expression vector comprising a nucleic acid sequence coding for the particular protein. The host cells are cultured under conditions whereby the nucleic acid sequence coding for the particular protein is expressed. After a suitable amount of time for the product to accumulate, the protein is purified from the host cells or medium surrounding the cells.

Host cells and expression vectors suitable for use in the invention are chosen to form an expression system capable of producing the α-1-antichymotrypsin or α-1-antichymotrypsin analogue product. Host cells suitable for use in the invention include prokaryotic and eukaryotic cells that can be transformed to stably contain and express α-1-antichymotrypsin. Suitable types of cells include bacterial, yeast and mammalian cells. When prokaryotic host cells are used, no glycosylation of α-1-antichymotrypsin or analogue will occur. The bacterium E. coli is preferred for the production of the protein products. Cloning and expression can be obtained rapidly in E. coli. Production in E. coli is readily amenable to cost-effective, large-scale fermentation and protein purification. Introduction of an expression vector incorporating a nucleic acid sequence coding for human α-1-antichymotrypsin or analogue into a host cell can be performed in a variety of ways, such as calcium chloride or lithium chloride treatment or electroporation.

The expression vector comprising the nucleic acid sequence coding for human α-1-antichymotrypsin preferably further comprises transcription and translation control elements operatively linked to the nucleic acid sequence coding for human α-1-antichymotrypsin; for example, in an upstream position, a promoter, followed by a translation initiation signal comprising a ribosome binding site, and an initiation codon, and, in a downstream position a transcription termination signal. The transcription and translation control elements may be ligated in any functional combination or order. The transcription and translation control elements used in any particular embodiment of the invention will be chosen with reference to the type of cell into which the expression vector will be introduced, so that an expression system is created.

It is preferable to use a strong promoter, such as the E. coli trp-lac promoter or the T7 $P_L$ promoter, to ensure high levels of expression of the protein product. The plNomp and β-lactamase promoters have been found to give low or no yields of α-1-antichymotrypsin when operatively linked with DNA coding for α-1-antichymotrypsin. It is also preferable that the promoter is an inducible promoter, such as the $P_L$ promoter, to avoid possible host cell toxicity during accumulation of the product.

Alternatively a gene expression system based on bacteriophage T7 RNA polymerase as disclosed in Studier and Moffatt, J. Mol. Biol. 189: 113-130, (1986), which is specifically incorporated as if fully set forth herein, may be used. In this system, E. coli cells transformed with plasmids containing the bacteriophage T7 promoter operatively linked with a DNA sequence coding for a selected product are infected with lambda phage having an expressible gene for T7 RNA polymerase. The cells are infected with phage after sufficient copies of the plasmids are present in the host cells and protein synthesis appears soon after infection.

Transformed host cells containing a DNA sequence coding for human α-1-antichymotrypsin or analogue may then be grown in an appropriate medium for the host. Where an inducible promoter is employed, the host cell may be grown to high density and the promoter turned on for expression of the fusion protein and protease. Where the promoter is not inducible, then constitutive production of the protein product will occur. Constitutive production of α-1-antichymotrypsin or analogue is preferable only in expressions systems where it is not substantially toxic to the host cell. The cells may be grown until there is no further increase in product formation or the ratio of nutrients consumed to product formation falls below a predetermined level, at which time the cells may be harvested, lysed and the protein product obtained and substantially purified in accordance with conventional techniques. Such techniques include chromatography, electrophoresis, extraction, and density gradient centrifugation.

Proteins having an amino acid sequence containing more or fewer amino acids, fragments, or differing by one or more amino acids from the sequence of α-1-antichymotrypsin or analogues as disclosed herein that have antichymotrypsin, anti-trypsin or antithrombin activity are also within the scope of the invention. Correspondingly, nucleic acid sequences coding for these proteins are also within the scope of the invention.

A human gene coding for α-1-antichymotrypsin can be readily obtained from a human liver cDNA library. Suitable is libraries can be obtained from commercial sources such as Clontech, Palo Alto, Calif. Alternatively, a cDNA library can be prepared from RNA isolated from a human liver. The cDNA library is screened with a suitable probe, such as an antibody specific for α-1-antichymotrypsin or Cl esterase inhibitor, using conventional techniques. Positive cells are then subjected to DNA sequencing to determine the presence of a DNA sequence coding for α-1-antichymotrypsin. DNA sequencing is readily accomplished using the chain termination method of Sanger et al., Proc. Natl. Acad. Sci. USA 74: 5463-5467, (1977). DNA sequences coding f or the entire human serum α-1-antichymotrypsin molecule, and antichymotryptically active DNA sequences, which may be shorter or longer than the DNA sequence coding for the serum protein, are suitable for use in the invention. The DNA sequence coding for α-1-antichymortrypsin is then inserted into an expression vector for later expression in a host cell.

The α-1-antichymotrypsin, analogues and protein preparations of the invention are expected to be useful for treatment of septic shock, pancreatitis, coagulation disorders as in liver diseases, certain diseases caused by microbes that penetrate the skin by elaborating a microbial chymotrypsin-like enzyme and skin inflammation in mammals, including humans. The compositions of the invention may be administered to mammals, including humans by various routes, including intravenous, intramuscular, intraperitoneal routes, and topically to an affected area of the skin. The compositions of the invention are preferably delivered to the affected mammal in combination with a physiologically acceptable liquid, such as a saline solution or other buffer, or physiologically acceptable carrier. Suitable pharmaceutical carriers are well known in the art and described, for example, in Remington's Pharmaceutical Sciences, E. W. Martin, a standard reference text in this field. For treatment of skin inflammation, the compositions of the invention may be applied to the affected area in combination with a physiologically acceptable ointment or cream. The particular amount of the compositions of the invention that will be administered to the mammal for any particular condition will depend on the type of illness, and other factors such as the weight and age of the patient and route of delivery. For topical applications, the compositions of the invention are applied in an amount effective to reduce or inhibit worsening of skin inflammation.

Experimental

Cloning and Sequencing of the Gene for Antichymotrypsin

Materials and Method,

Isopropyl-$\beta$-thiogalactopyranoside (IPTG), EcoRl, Pstl, Hindlll, calf intestinal alkaline phosphatase, T4 DNA polymerase, mung bean nuclease, Klenow fragment, pUC19, and pKK233 were obtained from Promega (Madison, Wis.). Diaminobenzidine, DNA cellulose, bovine pancreatic chymotrypsin and trypsin, and all chromophoric protease substrates were obtained from Sigma (St. Louis, Mo.). DH5, JM101, and JM105 cells were obtained from the Cell Center of the University of Pennsylvania. plNomp/NcoI/b, a secretion vector that allows fusion of a cloned protein to the omp leader peptide, was obtained from Professor John Collins and Dr. Gerhard Gross (Gesellschäft für Biotechnologische Forschung, Braunschweig, FRG).

Human serum $\alpha$-1-antichymotrypsin was prepared using a procedure based on the work of Tsuda et al., Tokai. J. Exp. Clin. Med. 7: 201-211, (1982). This method affords pure $\alpha$-1-antichymotrypsin in three steps, batchwise elution from DNA cellulose, G-150 chromatography, and CaCl gradient elution from DNA cellulose.

Plasmid constructions and DNA manipulations were carried out following Maniatis et al., Molecular Cloning: A Laboratory Manual, Cold Spring Harbor Laboratory Press, Cold Spring Harbor, N.Y., (1982).

Identification and sequencing of the gene from human antichymotrypsin

A human liver cDNA library in the phage expression vector lambda-gtll provided by Mitchell Weiss, Department of Human Genetics, University of Pennsylvania, was screened according to the method of Young and Davis, Proc. Natl. Acad. Sci. 80: 1194-1198, (1983), with polyclonal antisera raised against Cl esterase inhibitor (DAKO, Santa Barbara, Calif.), a related human serine protease inhibitor. Positives were picked, rescreened and plaque-purified. DNA sequencing was performed with the chain termination method of Sanger et al., Proc. Natl. Acad. Sci. U.S.A. 74: 5463-5467, (1977), using oligonucleotide primers obtained from the Nucleic Acid Synthesis Center of the Wistar Institute (Philadelphia, Pa.).

The DNA sequence and the derived amino acid sequence of the insert from one of the positive lambda-gtII cDNA clones contained the entire coding region of the mature human $\alpha$-1-antichymotrypsin. The insert also included a 12 nucleotide extension of the 5'-end encoding four amino acids that appear in the precursor of the mature protein, as shown in FIG. 1$a$ within the boxed area. The mature protein contains 398 amino acids (Mr 45,031) starting from the tripeptide AsnSerPro (FIG. 1$a$) at the amino terminus and contains a single cysteine residue at position 236. The reactive center, P1-P1', Leu-Ser, is found at positions 358-359 and is shown in FIG. 1 within the boxed area. The C-terminal sequence is in agreement with Hill et al., Nature 311:175-177, (1984) and the remainder of the sequence is in agreement with Chandra et al., Biochemistry 22: 5055-5060, (1983) except for the 15 amino acids from position 77 to 91 and the 6 amino acids from 98 to 103. These differences can be explained by three insertions and three deletions of single bases within the Chandra sequence. The sequence reported here retains a high degree of similarity with $\alpha$-1 protease inhibitor in this region and raises the overall identity with $\alpha$-1-protease inhibitor by 17 residues, to 44.5%. In addition, the sequence shows a proline at position 44 rather than a leucine, a leucine at 174 rather than a proline, an alanine for valine at 336 and a leucine for serine at 338. The latter two amino acid substitutions have been reported by Hill et al, supra. A second form of mature protein that includes two additional amino acids, His-Pro, at the N-terminus (FIG. 1) has also been found.

Expression Systems

The EcoR1 insert from the recombinant lambda-gtll was subcloned into pUC19 (Promega, Madison, Wis.). pKK233 (Promega, Madison, Wis.) was digested with HindIII, the overhanging ends were filled in by treatment with Klenow fragment in the presence of the four deoxynucleotide triphosphates, and dephosphorylated with alkaline phosphatase. The EcoR1-EcoR1 fragment containing the entire antichymotrypsin coding sequence was removed from the pUC19 vector, isolated by agarose gel electrophoresis, treated with mung bean nuclease to generate a blunt end fragment in the correct reading frame and ligated to the modified pKK233 vector described above, to form the recombinant vector pKKAcT. PKKACT yields the recombinant protein denoted rACT-1.

A heat-inducible, high-expression vector denoted pT7PL was prepared by first placing the Shine-Dalgarno sequence and start codon from the T7 vector pAR3039 upstream to the coding sequence of the antichymotrypsin gene and then placing the gene with these heterologous regulatory sequences under the control of the PL promotor in pKC30. The recombinant was denoted pACT2 and yielded recombinant protein denoted TACT-2. The construction is shown in FIG. 2.

pKT280 (Clontech, Pal Alto, Calif.) was digested with Pstl, phenol/chloroform extracted and ethanol precipitated. The 3' overhanging ends were removed with T4 DNA polymerase using 2U enzyme/mg DNA in the presence of 3.3,mM dNTps. The vector was then treated with calf alkaline phosphatase. The EcoRl-EcoRl fragment containing the entire antichymotrypsin coding sequence was isolated by agarose gel electrophoresis and the 5' overhanging ends filled in with Klenow fragment as described above. The resulting DNA was blunt-end ligated to the vector prepared as described, yielding the recombinant vector pKTACT.

Four different E. coli vectors, two secretion systems (pINomp/NcoI/b and pKT280) and two non-secretion systems (pKK233 and pT7PL), were evaluated for expression of recombinant human antichymotrypsin. More than 100 recombinants in a modified pINomp vector were screened and yielded plasmids with the insert in the wrong orientation in every instance, presumably because the correct orientation constructs lead to high level production of a toxic gene product. A second secretion plasmid, pKT280, in which expression is driven from the β-lactamase promoter and which encodes part of the signal sequence of β-lactamase, was also examined. The construct yielded full length ACT in low yield with an amino terminal extension coding for an additional eight amino acids, his-pro-gin-phe-leu-cys-his-pro, the first four originating from the vector and the following four from the precursor of antichymotrypsin.

The expression plasmid pKK233, utilizes the strong trp-lac promotor yielded a recombinant protein, migrating with an apparent $M_r$ of 45,000, that could be detected on Western blots of crude extracts, using affinity-purified antibody raised against α-1- antichymotrypsin. The construction of the expressed protein contains an amino terminal extension of ten residues, met-ala-ala-ala-lys-leu-leu-lys-his-pro-asn.

The highest level of expression was obtained with pACT2, which utilizes the PL system shown in FIG. 2.

Site-directed Mutagenesis For Synthesis of α-1-antichymotrypsin Analogues

Site-directed mutagenesis of the DNA sequence coding for α-1-antichymotrypsin was carried out using a commercially available kit (BioRad (Richmond, Calif.) M13 Mutagenesis Kit) according to the manufacturer's instructions and the synthetic DNA primers (5'-CTAATGCAGACATGAGGGTGATT-3' for L358M to substitute a methionine at position 358 for leucine and 5'-TGCAGAACGGAGGGT-3' for L358SR to substitute an arginine at position 358 for leucine). The synthetic DNA primers was synthesized using standard techniques. The altered genes were excised from double-stranded M13 with EcoRl and inserted into pKK233 as described for the wild-type (α-1-antichymotrypsin) construction, yielding recombinants denoted PKKACT-M and PKKACT-R for the methionine and arginine mutants, respectively. Both mutations were confirmed by DNA sequencing. The corresponding proteins were denoted L358M-rACT-1 and L358R-rACT-1, respectively. Wild-type refers to the native form of α-1-antichymotrypsin.

To make the cassette protein site directed mutagenesis of the DNA sequence coding for α-1-antichymotrypsin was carried out using a commercially available kit (BioRad (Richmond, Calif.) M13 Mutagenesis Kit) according to the manufacturer's instructions and the synthetic DNA primers 5'-GTTGAAACGC-GTAATGGTCCTT-3' to construct a Mlu I restriction endonuclease site and 5'-ACTGCTGTGGTAC-CAGATGCTTC-3' to create a Kpn I restriction endonuclease site. The synthetic primers were synthesized using standard techniques. The altered gene was excised from double-stranded M13 with EcoRl and inserted into pKK233 as described for the wild-type (α-1-antichymotrypsin) construction, yielding the recombinant denoted PACTCAS. The Kpn I and Mlu I restriction sites are unique to the DNA sequence. Creating the Kpn I restriction at positions corresponding to amino acids 349 and 350, as shown in FIG. 1d changing Ala-Ala to Gly-Thr and creating the Mlu I restriction site at positions corresponding to 368 and 369 changing Val-Arg to Thr-Arg. The region between the restriction sites, i.e. the cassette, contains the active site of α-1-antichymotrypsin and can be removed with Kpn I and Mlu I to insert a desired DNA sequence.

The α-1-antichymotrypsin analogue having phenylalanine substituted for leucine at position 358 was constructed by removing the cassette from PACTCAS by digestion with Kpn I and Mlu I and inserting synthetic DNA sequences having the following sequences 5'CA-CAGCAGTCAAAATCACCCTCTTCTCTGCAT-TAGTGGAGACAAGGACCATTA-3' and 5'CGCGTAATGGTCCTTGTCTCCACTAATG-CAGAGAAGAGGGTGATTTTGACTGCTGTG-GTAC-3' to form a new recombinant plasmid denoted PACTCASPHE, where each single strand is synthesized by standard techniques and the double stranded insert is formed by annealing the two single strands. This insert is then ligated into the Kpn I-Mlu I site.

Small-scale growth conditions and extraction

Fresh overnight cultures of JM 105 transformed with PKKACT, PKKACT-M or PKKACT-R were diluted to 1.5% in LB broth containing H ampicillin (Na salt, 0.1 mg/ml) and grown to an $A_{600nm}$ of 0.3, induced with 1.25mM IPTG and grown for an additional five hours. The cells were pelleted and then disrupted in a French press. The ACT proteins purified from these transformed cells are denoted TACT-1, L358M-rACT-1, and L358R-rACT-1, respectively.

Fresh overnight cultures of N4830-1 were transformed with pACT2, grown overnight at 30° C., diluted to 1% in LB broth containing ampicillin (Na salt, 0.1 mg/ml) and grown to an $A_{600nm}$ of 0.2, then shifted to 42° C. and grown for an additional five hours at 42° C. The cells were pelleted and disrupted as above. The ACT protein purified from this transformed cell is denoted rACT-2.

Fresh overnight cultures of DH-5 cells transformed with PKTACT were diluted to 1.5% in LB broth containing ampicillin (Na salt, 0.1 mg/mL), grown for seven hours, and harvested by centrifugation. The washed cell pellet was suspended in 20% sucrose, 50mM Tris (pH 7.5), 10mM EDTA, shaken for 7 min. at room temperature, and centrifuged at 13,000xg for 10 min. The pellet was rapidly resuspended in double-distilled water, and frozen, thawed and sonicated three times. The resulting mixture was centrifuged at 13,000xg for 10 min. and the supernatant was saved.

Western Blots

Commercial antisera (DAKO) were absorbed prior to use according to the following method. An overnight culture of E. Coli strain JMIOL (200 ml) was pelleted for 5 min at 4° C., rinsed with phosphate-buffered saline (PBS), resuspended in 6 ml of cold PBS and then frozen and thawed three times in dry ice-ethanol. The resulting mixture was sonicated six times for 30 seconds each and pelleted in a microcentrifuge at room temperature for 5 min. The supernatant was then diluted to 2% in PBS. 1.5 mls of 2% supernatant was added to a piece of nitrocellulose paper cut in 2.5×2.5 cm squares. This mixture was shaken at room temperature for 1 hr. The nitrocellulose was then rinsed twice in PBS. The E. coli extractsaturated paper was added to 20 mL of rabbit anti-antichymotrypsin serum, diluted 1:600 in Blotto (2% dry milk in 1.0% Triton, 0.05M Tris, 10.0mM EDTA) and swirled for 1 hr at room temperature. Proteins were transferred to nitrocellulose paper following the procedure of Tobin et al. (1979) Proc. Natl Acad. Sci. USA 76: 4350–4354. The resulting Western blots were stained using a staining kit (ABC Vectastain kit, Vector Laboratories, Burlingame, Calif.) and the color was developed with diaminobenzidine.

Antichymotryrsin activity Assays

Antichymotrypsin activity could not be directly measured in crude bacterial lysates because of a large background inhibitory activity in the lysate itself. The background activity was separated from the antichymotrypsin by anion exchange chromatography using a Mono Q HR5/5 anion exchange FPLC column (Pharmacia) fitted into a pump (LKB 2150 pump), 2152 gradient controller, and a UV absorbance detector (Waters 440 UV absorbance detector) with an extended wavelength module. Chromatography was typically conducted on the extract from 200 mg of cells. The separation involved an socratic wash (5 min) with 50 MM Tris-Cl buffer, pH 7.5, containing 50 mM KCl, followed by a linear gradient of KCl (50–350 mM in 30 min) at a flow rate of 1.0 mL/min. Protein absorbance was monitored at both 214 and 280 nm. Fractions (1.0 mL) were collected and assayed for ACT or antitrypsin activity measured as the inhibition of the chymotrypsin-catalyzed hydrolysis of substrate N-suc-Ala-Ala-Pro-Phe-p-nitroanilide (0.1 mL of a 10 mM solution in 90% DMSO), DelMar et al. (1979) Anal. Biochem. 22: 316–320, or of trypsin-catalyzed hydrolysis of substrate N-Bzl-Pho-Phe-Arg-p-nitroanilide (0.02 mL of a 14.6 mM solution in 90% DMSO) A typical chymotrypsin assay contained (in 1.0 mL):100 MM Tris-Cl buffer, pH 8.3, 0.005% (v/v) Triton X-100, bovine pancreatic chymotrypsin (18 mmole) and column eluate (0.005- 0.5 mL). The assay mixture was preincubated at room temperature for 5 min, substrate (0.01 mL of a 10mM solution in 90% DMSO) was added, and remaining chymotrypsin -activity was determined by the rate of change in $A_{410nm}$ caused by the release of p-nitroaniline. A typical trypsin assay contained (in 1.0 mL) 100 mM Tris-Cl buffer, pH 8.3, 0.005% (V/V) Triton X-100, bovine trypsin (8.6 pmol) and sample (0.005–0.5 mi). The assay mixture was preincubated at room temperature for 10 min, substrate (0.02 mL of a 15 MM solution in 90% DMSO) was added, and remaining trypsin activity was determined as above. Measurements of optical absorbance were conducted at 25° C. using a spectrophotometer (Hewlett Packard 8452A) fitted with a temperature controlled sample compartment.

The amount of active TACT-1, TACT-2, or L358M-rACT-1 present was determined by titration of a solution of chymotrypsin of known concentration and activity with varying amounts of partially purified TACT fractions. The amount of active chymotrypsin present after incubation with the inhibitor-containing solutions was then determined using the chymotrypsin activity assay. The amount of active L358R-rACT-1 present was determined in a similar manner by titration of a solution of trypsin of known concentration, using the trypsin activity assay. Concentrations of chymotrypsin and trypsin were determined using the active-site titration method of Ardelt and Laskowski (1985) Biochemistry 24: 5313–5320.

Purification and characterization of recombinant antichymotrypsins

Large-scale Growth of E. coli. E. coli JM105 strains were grown to a density of 4–5 $A_{550nm}$ in LB media containing ampicillin (Na salt, 0.1 m/mL) and glucose (0.1% w/v) at 37° C. in a 15L carboy fitted with an oxygen biabbler. Cells were harvested by passage through a Sharpless continuous-flow centrifuge. 3.5–5 g of cell paste (wet weight) were obtained per liter of culture. E. coli N4830-1 transformed with pACT2 was grown in LB medium containing ampicillin (Na salt, 0.1 m/mL) in a 15L carboy fitted with a heating coil, sampling tube, temperature probe, and an air bubbler. The media was inoculated with an overnight culture (200 mL) that had been grown at a constant temperature of 30° C. Growth was continued at 30° C. for one hour until the culture had reached an $A_{600nm}$ of 0.17. The temperature of the medium was shifted to 42° C. by pumping steam through the heating coil for a period of two minutes and then maintained at that temperature by a heating circulation bath for six hours until the culture had reached an $A_{600nm}$ of 0.9. The cells were harvested with a centrifuge as described above. 1.2 grams of cell paste (wet weight) were obtained per liter of culture.

Extraction and Column Chromatographies

Purifications of rACT-t, rACT-2, L358M-rACT-1 and L-358R-rACT-1 were all carried out in an essentially identical manner, with the exception that in the latter case an antitrypsin rather than an antichymotrypsin assay was used to detect and quantitate recombinant inhibitor. All purification steps were carried out at 4° C. In a typical preparation of r-ACT-1, cell paste (3.1 g) was dispersed in 10mM potassium phosphate buffer, pH 6.9 (25 mL) and lysed by three passes through a French press at 10,000 psi and 4C. Cell debris was removed by centrifugation at 30,000 xg for 30 min at 4° C. The supernatant (25 mi) was loaded onto a column (4.9 cm$^2$ ×37 cm) of Sepharose Fast Q (Pharmacia) that had been equilibrated to 50mM Tris-Cl, pH 7.5, containing 50 mM KCl. Protein eluted with a linear gradient of KCl in 5OmM Tris-Cl, pH 7.5 (50–500mm in 2 L). H Fractions (15 mL) were monitored for protein by $A_{280nm}$ and assayed for antichymotrypsin activity as described above. rACT-1 eluted at approximately 200mM KCl. Fractions #50–#58, containing TACT-1, were combined and dialyzed against two volumes (2.5 L each) of 10 MM potassium phosphate buffer, pH 6.9 over 48 h. The dialyzed solution was then applied to a DNA-cellulose column (1.7 cm$^2$ ×20 cm) that had been preequilibrated with 10 mM potassium phosphate, pH 6.9, containing 10 mM KCl. After loading, the column was first washed with the same buffer (20 mi). The column was eluted with a linear gradient of KCl (10–400mM, 300 mL) in the same buffer. Fractions (8 mL) were assayed for protein and antichymotrypsin activity as above. rACT-t eluted between 350mM and 400mM KCl (fractions #49–#53). Fractions containing antichymotrypsin activity were analyzed for purity by SDS-PAGE, performed according to Laemmli (1970) Nature (London) 227: 680–685. Fractions in the early portion of the antichymotrypsin peak showed a higher level of purity than those in the later portion. Each portion was concentrated by ultrafiltration using Amicon YM-10 membranes and dialyzed overnight against 50 mM Tris-Cl, pH 7.5 (500 mL). In some cases recombinant proteins were further purified on an FPLC Mono Q anion exchange column, using the conditions described above.

Automated Edman peptide sequence analysis on rACT-2 (using the Milligem/Biosearch 6600 Series Prosequencer of the Protein Facility of the Dental School of the University of Pennsylvania) yielded a sequence in full accord with that predicted in FIGS. 1a through 1e beginning with the tripeptide AlaSerMet.

The purifications of rACT-1 and rACT-2 are slimmarized in Table I, from which it is clear that much higher levels of expression are achieved with the second expression system (pT7PL). In both cases, SDS-PAGE analysis of protein gradient-eluted from the DNA-cellulose column (see Methods) showed a single band with a molecular weight of approximately 45,000 daltons. Purification results similar to those for rACT-t were obtained for L358M-rACT-1 and L358R-rACT-1.

TABLE 1

Purification of Recombinant Antichymotrypsin from two *E. coli* Expression Systems

| Step | Antichymotrypsin (mg)[a] | Total Protein (mg)[b] | Yield (%) | Purification Factor |
|---|---|---|---|---|
| 1) *E. coli* pKKACT (2-45-32)[d] | | | | |
| Crude lysate | 0.47[d] | 300 | 100 | — |
| Fast Q | 0.41 | 33 | 86 | 7.9 |
| DHA-cellulose | 0–20 | 0–30 | 42 | 430 |
| 2) *E. coli* pT7PL[a] | | | | |
| Crude lysate | N.D.[f] | 2500 | — | — |
| Fast Q | 132 | 880 | 100 | — |
| DHA-cellulose | 107 | 122 | 81 | 5.8 |

[a]The amount of antichymotrypsin was determined by titration of bovine chymotrypsin as described in the methods section.
[b]The amount of total protein was determined using the method of Bradford (43).
[c]from 3.1 g of cell paste (wet weight).
[d]The amount of antichymotrypsin in the crude lysate was estimated using Mono Q chromatography followed by titration as described in Materials and Methods.
[e]from 19.1 g of cell paste (wet weight).
[f]Not determined Inhibition of Serine Protease Activity by Recombinant Antichymotrypsins The rates of inhibition by human serum ACT, TACT-1, TACT-2, L358M-rACT-1, and L358R-rACT-1 of bovine chymotrypsin, bovine trypsin, human thrombin, porcine pancreatic elastase, and human neutrophil elastase were investigated at 25° C. under second-order conditions, in reaction mixtures containing equimolar concentrations of enzyme and inhibitor, or under pseudo-first order conditions with an excess of inhibitor. As described above, enzyme and inhibitor were incubated in 100 mM Tris-Cl buffer, pH 8.3, containing 0.005% (v/v) Triton X-100 for varying periods of time, substrate was then added, and the amount of remaining active enzyme was determined. Alternatively, at timed intervals aliquots of the inhibitor plus enzyme solution were diluted into an assay solution containing the appropriate substrate and protease activity was determined.

Both human serum and recombinant ACTs were tested for their inhibitory activities toward several serine proteases, giving the results summarized in Table 2. The various antichymotrypsin serine protease pairs fall into three groups. The first group comprises those pairs in which full ($>90\%$) inhibition was observed at a 1:1 ratio of inhibitor to protease. Examples of such pairs are bovine chymotrypsin with either human serum ACT, TACT-1, or TACT-2. Second-order plots of rate data for inhibition with human serum ACT and rACT-1 demonstrate that both second-order rate constants are identical ($8 \times 10^5$ M$^{-1}$s$^{-1}$ - the corresponding value determined with rACT-2 was $6 \times 10^5$ M$^{-1}$s$^{-1}$). Essentially the same rate constant using both the assay conditions described herein in "Kinetics of Complex Formation" supra and that of Beatty et al., J. Biol. Chem. 255:3931-3934, (1980). Independent measurements using a third set of assay conditions (phosphate-buffered saline) also yielded an association rate constant on the order of $4 \times 10^5$ M$^{-1}$s$^{-1}$ at 25° C. These values are an order of magnitude higher than the value of $6 \times 10^4$ M$^{-1}$s$^{-1}$ previously determined by Beatty et al., supra for reaction of human serum α-1-antichymotrypsin with bovine chymotrypsin at 25° C. The reasons for this apparent disagreement are unclear.

In the second group of pairs, full inhibition required a stoichiometric excess of inhibitor over protease. Chymotrypsin and L358R-rACT-1 and pancreatic porcine elastase and either human serum ACT, TACT-1, or rACT-2 fall into this group. The degree of final inactivation, as a function of the ratio of L358R-rACT-1 to chymotrypsin and of rACT-2 to porcine pancreatic elastase, shows that full inactivation is achieved at extrapolated ratios of 2.2 and 2.5, respectively. Very similar results were obtained when human serum ACT was used in place of TACT-2. This second group of pairs is considered further below.

The third group of antichymotrypsin:protease pairs showed no detectable inhibition ($<3\%$), allowing estimation of only upper limits of second-order rate constants. The estimates presented in Table 2 are based upon the simple second order kinetic scheme described by Beatty supra, the concentration of enzyme and inhibitor used, the total length of time allowed for the reaction (usually 45-240 min), and assuming a threshold level for detection of inhibition of a 10% loss of protease activity.

TABLE 2

Interaction of Recombinant Antichymotrypsins and Serine Proteases. Formation of SDS-Stable Complexes[a] and Inhibition Rate Constants (measured at 25° C., pH 8.3)

| Enzyme | Substrate (final molarity) | rACT-1 or rACT-2 (molarity)[b]$K_a$[c] | L358M rACT (molarity)[b]$K_a$[c] | L358R rACT (molarity)[b]$K_a$[c] |
|---|---|---|---|---|
| bovine chymotrypsin | Suc—A—A—P—F p-nitroanlide (0.2 mM) | 9 nM, 6–8 × 10$^5$(+) 18 nM | 18 nM 3 × 10$^5$ | 72 nM 1 × 10$^4$(+) 360 nM [2.2 × 10$^4$][d] |
| trypsin | N—p-Tos—G—P—R p-nitroanlide (0.2 mM) | 172 nM <5 × 10$^2$(−) | 172 nM <10$^2$(−) | 8.6 nM 5.4 × 10$^5$(+) |
| human thrombin | N—p-Tos—G—P—R p-nitroanlide (0.2 mM) | 425 nM <3 × 10$^2$(−) | 213 nM <10$^3$(ND) | 850 nM 4.3 × 10$^3$(+) |
| porc. panc. elastase | Suc—A—A—A— p-nitroanilide (1.0 mM) | 480 nM[e] 8.0 × 10$^3$(+) 960 nM[f] [2.0 × 10$^4$][d] | 193 nM <10$^3$(+) | 770 nM <10$^2$(ND) |
| human neut. | Suc—A—A—P—V— | 207 nM <10$^3$(ND) | 207 nM <10$^3$(+) | 800 nM <10$^2$(ND) |

TABLE 2-continued

Interaction of Recombinant Antichymotrypsins and Serine Proteases. Formation of SDS-Stable Complexes[a] and Inhibition Rate Constants (measured at 25° C., pH 8.3)

| Enzyme | Substrate (final molarity) | rACT-1 or rACT-2 (molarity)[b]$K_a$[c] | L358M rACT (molarity)[b]$K_a$[c] | L358R rACT (molarity)[b]$K_a$[c] |
|---|---|---|---|---|
| elastase | p-nitroanlide (1.0 mM) | | | |

EXPLANATION OF TABLE 2
[a](+), DSD-stable complex formed,; (−), SDS-stable complex not formed; (ND), not determined.
[b]Equimolar concentrations of enzyme and inhibitor were reacted, unless noted otherwise. The concentration of wild-type recombinant inhibitor and of the L358M mutant inhibitor were both determined by titration with bovine chymotrypsin. The concentration of the L358R mutant inhibitor was determined by titration with bovine trypsin.
[c]$M^{-1}s^{-1}$
[d]Corrected for partitioning of the (E.I.)$_a$ complex. See text.
[e]The association rate constant of rACT with porcine pancreatic elastase was determined under pseudo-first order conditions with an enzyme concentration of 24 nM. The rate constant for reaction with human serum ACT was $6.9 \times 10^3 M^{-1}s^{-1}$.
[f]Determined under pseudo-first order conditions with an enzyme concentration of 48 nM.

Formation of SDS-Stable Complexes Between Recombinant Antichymotrypsins and Serine Proteases The complex that human serum ACT forms with chymotrypsin is stable in SDS polyacrylamide gels and migrates at a higher molecular weight than ACT itself. Western blots of Laemmli gels were used to determine whether or not SDS-stable complexes are formed between TACT (and TACT variants) and proteases, giving the results summarized in Table 2. The complexes themselves appear to be substrates for the corresponding uncomplexed proteases, since they are readily degraded as the [protease]/[inhibitor] ratio is increased.

The formation of serine protease:rACT complexes was examined using either crude extracts containing rACTs or highly purified rACTs. In the former case, such experiments provided a useful screen for the expression of active protein. As the ability of an rACT analogue to form an SDS-stable complex with a protease correlates very well with its affording a measurable rate of protease inhibition, as shown in Table 2, it can be concluded that the mutant rACTs inhibit proteases by the same mechanism as does human serum ACT. The one apparent exception to the above noted correlation is the interaction between L358M-rACT-1 and porcine pancreatic elastase. Here evidence for complex formation was found but a rate of protease inhibition could not be measured. However, as inhibition from a rate constant that was more than ten-fold less than that for rACT-t could not be detected, this exception may be more apparent than real.

Effects of α-1-antichymotrypsin On Neutrophil Activity

Native ACT, isolated and purified from human serum, inhibited neutrophil $O_2$- production at physiologically relevant concentrations yet had no effect on neutrophil degranulation. ACT itself did not stimulate $O_2$- production nor did it effect $O_2$-generation in a xanthine-xanthine oxidase cell free system. ACT was not cytotoxic to neutrophils as assessed by lactic dehydrogenase leakage (<4%). ACT (8μM) markedly inhibited $O_2$-production (26% of controls) triggered by the chemotactic peptide FMLP ($10^{-7}$M) ; even at higher concentrations of this stimulus ($5 \times 10^{-6}$M) ACT produced a 75% inhibition. Inhibition of $O_2$-generation by ACT was dose dependent with half maximal inhibition at 3.5μM ACT. The effect of ACT was on the rate of $O_2$-generation and was without effect on onset or duration of the response. ACT also inhibited $O_2$- production stimulated by PMA (0.5μg/ml) and Con A (100 μg/ml) in a dose related manner. The inhibitory effects on ACT were potent; preincubation was not required and was effective even after the burst was initiated (addition of ACT (8μM) 1 min post FMLP ($10^7$M) reduced $O_2$-generation to 49% of controls).

Human TACT was cloned, expressed in E. coli and purified to homogeneity. rACT (4μM also inhibited $O_2$-production triggered by FMLP ($10^{-7}$M) but was not as potent an inhibitor as nativeACT (73% vs 59%) of controls, respectively).

ACT at an effective inhibitory concentration (8μM) had no effect on FMLP ($10^{-7}$M) stimulated releases of azurophil and specific granules as measured by β-glucuronidase and lysozyme release, respectively. In contrast to the lack of effect on release of granule enzymes, ACT inhibited endogenous chymotrypsin-like activity in intact neutrophils as measured by inhibition of the chymotrypsin-catalyzed hydrolysis of the substrate N-succinyl-ala-ala-pro-phe-p-NA. The role of this endogenous protease in regulating neutrophil function is unknown but may be involved in modulating $O_2$-generation. ACT may selectively alter neutrophil function through interaction with endogenous neutrophil proteases.

Summary

Recombinant α-1-antichymotrypsin disclosed herein surprisingly has the same or similar interactions with serine proteases and DNA as does the human serum protein, despite the fact that the recombinant protein is unglycosylated. Glycosylation accounts for approximately 30% of the total molecular weight of the serum protein. Evidence for the similarity of interaction with serine proteases is provided by 1) Western blot analyses showing formation of SDS-stable complexes of recombinant α-1-antichymotrypsin with both chymotrypsin and cathepsin G, but not with trypsin, and 2) the identity of rate constants of association of both recombinant and serum α-1-antichymotrypsins with chymotrypsin. Evidence that recombinant α-1-antichymotrypsin binds to DNA is provided by its strong retention on a DNA-cellulose column, a feature that was exploited in the purification procedure. Indications of the strength of such binding are that it occurs at a pH (6.9), at which α-1-antichymotrypsin has high negative charge (the human serum protein is acidic, with an isoelectric point between 4.2 and 5.0), and that elution of α-1-antichymotrypsin requires a quite high KCl concentration (similar to that required for the serum protein).

The human gene for α-1-antichymotrypsin has been cloned and expressed in E. coli, and purified as a biologically active recombinant produce. The α-1-antichymotrypsin should be useful in treatments such as those described herein, substituting for the native purified compound.

Novel α-1-antichymotrypsin analogues having antichymotrypsin activity, anti-trypsin and anti-thrombin have been made. These α-1-antichymotrypsin analogues have methionine, arginine or phenylalanine substituted for leucine at position 358.

The properties of L358R-rACT-1 support the conclusion arginine in the $P_1$ position is a major determinant of serpin specificity in both a positive and negative sense. This single amino acid change turns TACT into a serpin capable of inhibiting thrombin and trypsin, but having a considerably reduced (30-fold) rate of reaction with chymotrypsin. In fact, even though rACT and antithrombin III have only limited (28%) overall identity, the specificity of L358R-rACT-1 resembles that of antithrombin III (an inhibitor having an arginine in its $P_1$ position), and the rate constants for inhibition of thrombin by these two inhibitors are virtually identical, $4.3 \times 10^3 M^{-1}s^{-1}$ for L358R-rACT-1 (as shown in Table 2) and $2.5 \ 10^3 M^{-1}S^{-1}$ for antithrombin III measured by Holmes et al. (1987) Biochemistry 26:5133–5140, under similar conditions.

What is claimed is:

1. A method of producing an analogue of human α-1-antichymotrypsin wherein the amino acid corresponding to the leucine at amino acid position 358 of wild-type α-1-antichymotrypsin is substituted with arginine, said analogue exhibiting anti-thrombin activity and anti-trypsin activity, comprising culturing host cells transformed with a DNA sequence coding for said analogue in a liquid medium, so that said analogue is produced; and purifying said analogue from said host cells or said medium.

2. A method of producing an analogue of human α-1-antichymotrypsin wherein the amino acid corresponding to the leucine at amino acid position 358 of wild-type α-1-antichymotrypsin is substituted with methionine, comprising culturing host cells transformed with a DNA sequence coding for said analogue in a liquid medium to produce said analogue; and purifying said analogue from said host cells or said medium.

3. A method of producing an analogue of human α-1-antichymotrypsin wherein the amino acids corresponding to alanine-alanine at amino acid positions 349 and 350 of wild-type α-1-antichymotrypsin are substituted with glycine-threonine respectively to form a Kpn I restriction endonuclease site and the amino acids corresponding to valine-arginine at amino acid positions 368 and 369 of wild-type α-1-antichymotrypsin are substituted with threonine-arginine respectively to form a Mlu I restriction endonuclease site comprising culturing host cells transformed with a DNA sequence coding for said analogue in a liquid medium to produce said analogue; and purifying said analogue from said host cells or said medium.

4. The method of claim 3 wherein the amino acid corresponding to the leucine at amino acid position 358 of wild-type α-1-antichymotrypsin is substituted in said analogue with phenylalanine.

* * * * *